(12) United States Patent
Chung et al.

(10) Patent No.: US 8,106,017 B2
(45) Date of Patent: Jan. 31, 2012

(54) PEPTIDES FOR PROMOTING HAIR GROWTH AND IMPROVING WRINKLE AND COSMETIC COMPOSITIONS COMPRISING THE SAME

(75) Inventors: Yong Ji Chung, Gyeonggi-do (KR); Young Deug Kim, Gyeonggi-do (KR); Chung Ryul Kim, Gyeonggi-do (KR)

(73) Assignee: Caregen Co., Ltd., Gunpo-si, Gyeonggi-do (KR)

( * ) Notice: Subject to any disclaimer, the term of this patent is extended or adjusted under 35 U.S.C. 154(b) by 307 days.

(21) Appl. No.: 12/083,969

(22) PCT Filed: Oct. 24, 2006

(86) PCT No.: PCT/KR2006/004352
§ 371 (c)(1),
(2), (4) Date: Jun. 26, 2008

(87) PCT Pub. No.: WO2007/049905
PCT Pub. Date: May 3, 2007

(65) Prior Publication Data
US 2009/0054349 A1    Feb. 26, 2009

(30) Foreign Application Priority Data
Oct. 24, 2005    (KR) .................. 10-2005-0100390

(51) Int. Cl.
*A61K 38/08*    (2006.01)
(52) U.S. Cl. .................. 514/18.6; 514/18.8; 514/20.7; 514/21.7

(58) Field of Classification Search .................. None
See application file for complete search history.

(56) References Cited

U.S. PATENT DOCUMENTS
4,297,276 A    10/1981    Goldstein et al.

FOREIGN PATENT DOCUMENTS
WO    03/063775 A2    8/2003

OTHER PUBLICATIONS

Philp, D., et al., "Thymosin $\beta_4$ increases hair growth by activation of hair follicle stem cells", *The FASEB Journal*, vol. 18, pp. 385-387, (2004).
Philp, D., et al., "Thymosin $\beta_4$ promotes angiogenesis, wound healing, and hair follicle development", *Mechanisms of Ageing and Development*, vol. 125, pp. 113-115, (2004).

*Primary Examiner* — Christina Bradley
(74) *Attorney, Agent, or Firm* — The Nath Law Group; Joshua B. Goldberg; Mih Suhn Koh (57) ABSTRACT

The present invention relates to a peptide comprising a specific amino acid sequence possessing human thymosin β-4 (Tβ4) activities and its uses. The peptide of this invention has identical or similar functions or actions to human Tβ4 and its biological activity is almost identical to natural-occurring Tβ4. In addition, the peptide of this invention exhibits much higher stability and skin permeation than natural-occurring Tβ4. In these connections, the composition comprising the peptides of this invention can exhibit excellent efficacies on improvement in thymosin β-4-effective disorders or conditions. In addition, the peptide of this invention can be advantageously applied to drugs, cosmetics, toothpaste and compositions for mouth cleaning and caring, most preferably, cosmetics. Specifically, the peptide of this invention is advantageously applied to cosmetics for promoting hair growth.

8 Claims, 9 Drawing Sheets

Fig 1

Predicted Configuration

PEPTIDES FOR PROMOTING HAIR GROWTH AND IMPROVING WRINKLE AND COSMETIC COMPOSITIONS COMPRISING THE SAME

The Sequence Listing submitted in text format (.txt) on Sep. 13, 2011, named "SequenceListing.txt" (created on Sep. 7, 2011, 4.0 KB), is incorporated herein by reference.

BACKGROUND OF THE INVENTION

1. Field of the Invention

The present invention relates to a human thymosin β-4 (Tβ4)-mimicking peptide and its uses.

2. Description of the Related Art

Hair is an organelle of which growth is complicatedly regulated by various growth factors depending on the growth steps of hair follicles. The differentiation of hair follicles and the related hair cycle are generally divided into several stages: hair-growing anagen; catagen in which hair loss is observed; telogen in which hair growth is arrested; and new anagen in which new hair is generated and grows (Paus, R., et. Al and Cotsarelis, G. (1999) The biology of hair follicles. *N. Engl. J. Med.* 341, 491-497).

Anagen stage, in which hair is growing, is divided into two sub-stages: one is the step of starting to generate hairs to come out from hair bulbs to hair follicles, and the other is the step of forming stiff keratin in hair follicles. Hairs continue the self-growth until the catagen stage. The life span of hairs in the anagen stage ranges from 3 to 6 years. Hairs in the anagen stage occupy 80-90% of total hairs (100,000-150,000 hairs) and grow about 1-1.5 cm during one month.

In catagen stage after anagen stage, the metabolism of hairs becomes to be slower with maintaining the shape of hairs and hair grows slowly. In addition, keratin is not formed in this stage. The catagen stage continues for 1-1.5 months and occupies 1% of total hairs. Hair bulb is contracted to be divided into hair papilla, which are surrounded by hair follicles and in turn is mobilized to upper part. The cell division is shown to be arrested at this time.

In telogen stage, hair papilla are shrunk, hair follicle is gradually contracted, and the hair root is pushed upward to be finally removed (the part of the hair root is raised upward and the depth of hair follicles become to be decreased by ⅓). This stage is characterized by hair loss and continues for 3-4 months. Hairs in telogen stage occupy 4-14% of total hairs (occupies 30-40% after birth) and easily falls out by only strong combing or stimulus.

Lastly, at the new anagen, hair bulbs which is surrounded by hair follicles in the anagen stage, combines with hair papilla to induce the formation of new hairs. Afterwards, the new hairs push upward and naturally remove old hairs in the talogen stage.

The hair cycles described previously are unlikely to occur in the same pattern. Hair cycles can be varied depending on the conditions such as diseases, heredity, body conditions and age. For example, some abnormalities such as the new anagen with non-terminated telogen, the angen without terminal hairs and the entrance of catagen with soft terminal hairs may be found.

Furthermore, as the society becomes more complex, factors facilitating hair loss such as environmental pollution, stress and numerous chemical compounds gradually increase. Therefore, the number of people suffering from hair loss tends to increase.

However, compounds or substances capable of preventing evidently hair loss or promoting hair growth have not yet proposed. Accordingly, there remains a need in the art to develop novel substances to facilitate hair growth.

Figure 1:
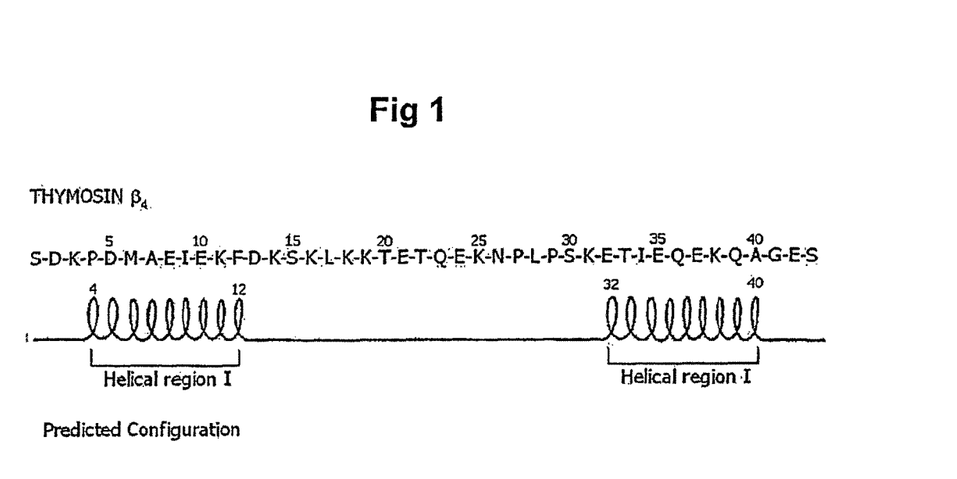
FIG. 1 represents the primary structure and putative secondary structure of thymosin beta-4 (Tβ4) (SEQ ID NO: 2).
Figure 2:
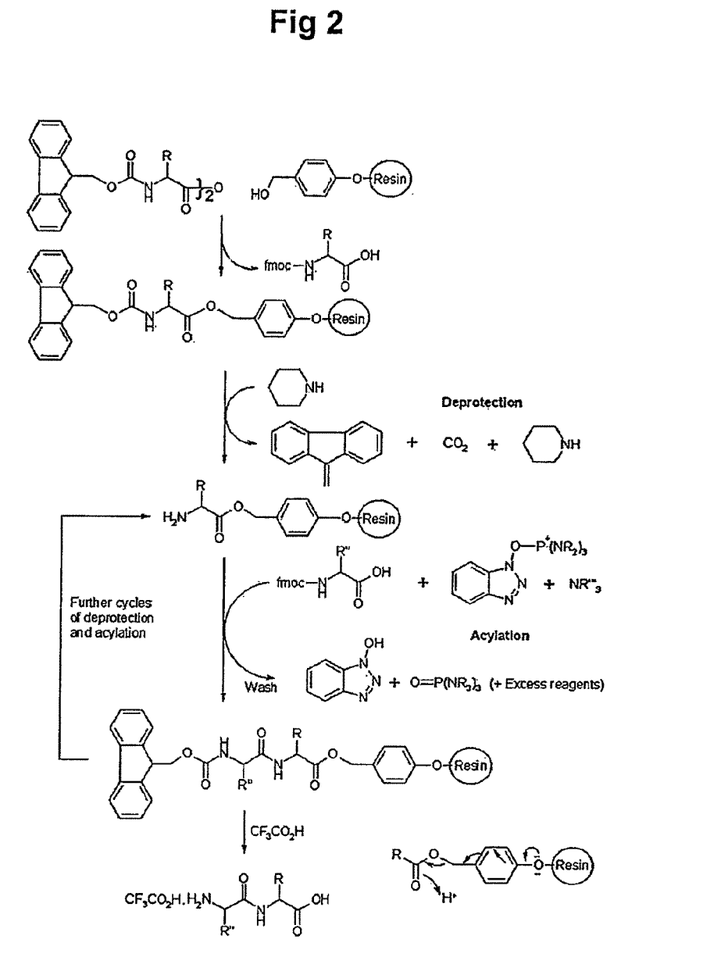
FIG. 2 schematically represents processes for synthesizing the exemplified peptide of this invention.

Thymosin beta-4 (Tβ4) has been discovered in cow thymus in the year of 1981. Tβ4 is a weakly acidic protein consisting of 44 amino acids having a molecular weight of 4.982 kDa, and having a theoretical isoelectric point of 5.1. Tβ4 has many polar amino acids such as glutamine and lysine residues. For example, Tβ4 has 11 aspartic acid and glutamine residues, and 9 lysine and arginine residues. FIG. 1 represents the putative secondary structure of Tβ4 comprising two helical structures.

It has been known to one of skill in the art that Tβ4 plays a crucial role as a regulator in cell migration and differentiation and is also involved in the wound healing and angiogenesis (Frohm, M., Gunne, H., Bergman, A. C., Agerberth, B., Bergman, T, Boman, A., Liden, S., Jornvall, H., and Boman, H. G. (1996) Biochemical and antibacterial analysis of human wound and blister fluid. *Eur. J. Biochem.* 237, 86-92).

However, a natural-occurring form of Tβ4 is very likely to show reduced treatment efficacies because such a form is neither biologically unstable nor physically homogenous. In addition, there is also a serious problem of relatively low skin permeation potency of Tβ4 in the natural form.

Accordingly, there remain long-felt needs to develop novel approaches for improving the stability and skin permeation of Tβ4.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

To overcome shortcomings of conventional technologies described above, the present inventors have made intensive researches to prepare and screen a variety of human thymosin β-4-derived peptides having the identical activities to naturally occurring Tβ4 and have selected a peptide showing superior activities and stability, eventually accomplishing the present invention.

Accordingly, it is an object of this invention to provide a peptide having the activities of human thymosin β-4 (Tβ4).

It is another object of this invention to provide a composition for preventing or treating a thymosin β-4-effective disorder or condition.

It is still another object of this invention to a method for preventing or treating a thymosin β-4-effective disorder or condition.

It is further object of this invention to provide a use of a peptide having the activities of human thymosin β-4 (Tβ4) for manufacturing a composition for preventing or treating a thymosin β-4-effective disorder or condition.

Other objects and advantages of the present invention will become apparent from the following detailed description together with the appended claims and drawings.

In one aspect of this invention, there is provided a peptide having the activity of human thymosin β-4 (Tβ4), which comprises the amino acid sequence of SEQ ID NO:1.

In another aspect of this invention, there is provided a composition for preventing or treating a thymosin β-4-effective disorder or condition, which comprises as an active ingredient the peptide of any one of claims 1-3 having the activity of human thymosin β-4 (Tβ4).

In still another aspect of this invention, there is provided a method for preventing or treating a thymosin β-4-effective disorder or condition, which comprises administering to a subject a composition comprising the peptide of any one of claims 1-3 having the activity of human thymosin β-4 (Tβ4) as an active ingredient.

In further aspect of this invention, there is provided a use of the peptide of any one of claims 1-3 having the activity of human thymosin β-4 (Tβ4) for manufacturing a composition for preventing or treating a thymosin β-4-effective disorder or condition.

The present inventors have made intensive researches to prepare and screen a variety of human thymosin β-4-derived peptides having the identical activities to naturally occurring Tβ4 and have selected a peptide showing superior activities and stability. Furthermore, the present inventors have prepared modified-peptides by modifying the amino acid sequence of human Tβ4-originated peptides having much better stability to physiochemical factors such as heat, acid and alkali.

The peptide of the present invention comprising the amino acid sequence of SEQ ID NO:1 is the actin-binding region of naturally occurring Tβ4.

The peptide of this invention comprises the human Tβ4-derived amino acid sequence of SEQ ID NO:1. Preferably, the peptide consists essentially of the amino acid sequence of SEQ ID NO:1. Most Preferably, the peptide consists of the amino acid sequence of SEQ ID NO:1.

The term used herein "peptide" refers to a linear molecule formed by linking amino acid residues through peptide bonds.

The peptides of the invention may be prepared by conventional chemical synthesis processes known to one of skill in the art, in particular, solid-phase synthesis techniques (Merrifield, *J. Amer. Chem. Soc.* 85:2149-54 (1963); Stewart, et al., *Solid Phase Peptide Synthesis,* 2nd. ed., Pierce Chem. Co.: Rockford, 111 (1984)).

The peptide of this invention has Tβ4-relating activities and shows in vivo functions and efficacies identical or similar to natural-occurring Tβ4. The term used herein "Tβ4-relating activities" refers to any and all activities of natural-occurring Tβ4 known to one of skill in the art, for example, including promotion of cell proliferation, angiogenesis and wound healing. Since the peptide of this invention is prepared to mimic the actions of natural-occurring Tβ4, it can exert all in vivo activities of natural-occurring Tβ4.

Because the peptide of this invention exhibits functions and actions identical or similar to natural-occurring Tβ4 and shows similar biological activities to natural-occurring Tβ4, it can be advantageously applied for preventing or treating thymosin β-4-effective disorders or conditions. As demonstrated in Experimental Example 1, the present peptide shows biological activities almost identical to natural-occurring Tβ4 (see FIG. 5).

The term used herein "thymosin β-4-effective disorders or conditions" refers to disorders or conditions able to be prevented or treated by natural-occurring Tβ4. Preferably, the activities addressing prevention or treatment efficacies of the present peptide may be described as anti-inflammatory activities, promotion of cell proliferation, promotion of biological activities of keratinocytes, wound healing, increase in biosynthesis of collagen, elastin, laminin and hyaluronic acid, treatment of periodontal disease, or improvement of skin conditions.

More preferably, the composition of this invention exhibits efficacies on the improvement in a skin condition. In particular, the peptides used as active ingredients in the present composition show excellent skin permeation because of their low molecular weight. Accordingly, where the present composition is topically applied to skin, it becomes evident that skin conditions are considerably improved. More still preferably, the improvement in the skin condition by the present composition includes the improvement in wrinkle or skin elasticity, the prevention of skin aging, the prevention of hair loss, the promotion of hair growth, the treatment of atopy, the improvement in skin moisture, the removal of dark spots or the treatment of acne, most preferably, the improvement in wrinkle or the promotion of hair growth.

For instance, the peptides used as active ingredients in the present composition promote the proliferation of fibroblasts or keratinocytes, induce the biosynthesis of procollagen, laminin, hyaluronic acid and fibronectin to regenerate keratinocyte layer, epidermis and dermis, thereby resulting in the improvements in wrinkle, skin elasticity and skin moisture, the prevention of skin aging and the treatment of atopic syndromes.

In addition, the peptide used as active ingredients in the present composition is very effective in the promotion of hair growth. As demonstrated in Experimental Example 5, the peptide allows to increase hair growth by 25-30% compared with control (untreated group) in animal model.

Even though the peptide of this invention per se has higher stability than natural-occurring Tβ4, its modification enables to have much higher stability. Preferably, the amino acid sequence of SEQ ID NO:1 has at least one amino acid residue protected with acetyl group, fluorenyl methoxy carbonyl group, formyl group, palmitoyl group, myristyl group, stearyl group or polyethylene glycol (PEG), most preferably, acetyl group.

The term used herein "stability" refers to in vivo stability and storage stability (e.g., storage stability at room temperature) as well. The protection group described above protects the peptides from the attack of protease in vivo.

More preferably, the amino acid residue protected with protection groups is one at either the N-terminal or C-terminal, most preferably the N-terminal (Lys residue). According to a preferred embodiment, —COOH of the Gln residue at the C-terminal of the peptide is modified to a hydroxyl group (—OH) or amino group (—NH$_2$) for enhancing stability.

Since the present peptide, preferably, modified peptide having protection groups are protected at its N- and/or C-terminal, their thermal stability at 37° C. is enhanced and their stability to physiochemical factors such as acid and alkali is also excellent. Therefore, since the peptides of this invention have significant long-term storage stability, they can be advantageously applied to products requiring long-term storage such as drugs, quasi-drugs, cosmetics and tooth/mouth cleaning or caring products.

The present composition may be prepared as a pharmaceutical or cosmetic composition.

According to a preferred embodiment, the composition is a pharmaceutical composition comprising (a) a pharmaceutically effective amount of the peptide comprising the amino acid sequence of SEQ ID NO:1; and (b) a pharmaceutically acceptable carrier.

The term used herein "pharmaceutically effective amount" refers to an amount enough to show and accomplish efficacies and activities of the peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, parenterally, e.g., by intravenous, intraperitoneal, intramuscular, subcutaneous, transdermal or local administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.0001-100 μg.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferred embodiment, the composition is a cosmetic composition comprising (a) a cosmetically effective amount of the peptide comprising the amino acid sequence of SEQ ID NO:1; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softener, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents, for example ethoxylated isostearyl alcohols, polyoxyethylene sorbitol esters and poly oxyethylene sorbitan esters, micocrystalline cellulose, aluminum metahydroxide, bentonite, agar and tragacanth or mixtures of these substances.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as peptides as active ingredients and carriers. The non-limiting examples of auxiliaries include preservatives, antioxidants, stabilizers, solubilizers, vitamins, colorants, odor improvers or mixtures of these substances.

The peptide used as active ingredients in the present invention has identical or similar functions or actions to human Tβ4 and its biological activity is almost identical to natural-occurring Tβ4. In addition, the peptide of this invention exhibits much higher stability and skin permeation than natural-occurring Tβ4. In these connections, the composition comprising the peptides of this invention can exhibit excellent efficacies on improvement in thymosin β-4-effective disorders or conditions. In addition, the peptide of this invention can be advantageously applied to drugs, cosmetics, toothpaste and compositions for mouth cleaning and caring, most preferably, cosmetics. Specifically, the peptide of this invention is advantageously applied to cosmetics for promoting hair growth.

The present invention will now be described in further detail by examples. It would be obvious to those skilled in the art that these examples are intended to be more concretely illustrative and the scope of the present invention as set forth in the appended claims is not limited to or by the examples.

EXAMPLES

Synthesis Example 1

Synthesis of Fmoc-Lys(Boc)-Leu-Lys(Boc)-Lys(Boc)-Thr(tBu)-Glu(tBu)-Thr(tBu)-Gln(trt)-CTL-resin 700 mg of chloro trityl chloride resin (CTL resin, Nova Biochem Cat No. 01-64-0021) were introduced into a reactor, to which 10 ml of methylene chloride (MC) were added, followed by agitation for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-Gln(trt)-OH and 400 mmole of DIEA were then added to the reactor, after which the mixture was dissolved by agitation and reaction was then undertaken with agitating for 1 hr. After washing with excess of DCM/DMF (1:1), 10 ml of DMF were added to the resultant and agitation was performed for 3 min, followed by removing the solvent. 10 ml of a deprotection solution (20% piperidine/DMF) were added to the reactor and agitation for 10 min at room temperature and solution removal were performed. After adding the same volume of the deprotection solution, the reaction was undertaken for 10 min and solution was removed, followed by washing sequentially with DMF, MC and DMF to yield Gln-(trt)-CTL resins. 10 ml of DMF solution was added to a new reactor and then 200 mmole of Fmoc-Thr(tBu)-OH, 200 mmole of HoBt and 200 mmole of Bop were added, followed by agitation for solubilization. 400 mmole of DIEA was added to the reactor and agitation was carried out to dissolve all solid contents. The dissolved amino acid solution was introduced into the reactor containing the deprotected resin and reaction was undertaken with agitating for 1 hr at room temperature. Following the removal of the reaction solution, the resultant was agitated three times with DMF solution to remove unreacted residuals. A small amount of the reacted resin was taken to evaluate extent of reactions by Ninhydrine test. Using the 20% piperidine/DMF solution, the deprotection was performed twice in the same manner as described above to yield Thr(tBu)-Gln(trt)-CTL resin. After washing with DMF and MC, Ninhydrine test was carried out and the attachments of amino acids were performed as described above. Based on the amino acid sequence designed by the present inventors, Fmoc-Glu(tBu)-OH, Fmoc-Thr(tBu)-OH, Fmoc-Lys(Boc)-OH, Fmoc-Lys(Boc)-OH, Fmoc-Leu-OH and Fmoc-Lys(Boc)-OH were attached to resins. The prepared peptidyl resin was washed three times with DMF, MC and methanol, respectively and dried under nitrogen atmosphere, after which it was vacuum-dried under $P_2O_5$, finally giving Fmoc-Lys(Boc)-Leu-Lys(Boc)-Lys(Boc)-Thr(tBu)-Glu(tBu)-Thr(tBu)-Gln(trt)-CTL-resin.

Synthesis Example 2

Synthesis of Fmoc-Lys(Boc)-Leu-Lys(Boc)-Lys(Boc)-Thr(tBu)-Glu(tBu)-Thr(tBu)-Gln(trt)-Rink amide Resin 1.42 g (1 mmole) of Fmoc-Rink amide resin (Nova Biochem Cat No. 01-64-0013) was introduced into a reactor, to which 10 ml of methylene chloride (MC) were added, followed by agitation for 3 min. After removing solution, 10 ml of dimethylformamide (DMF) were added to the resultant and then agitation was carried out for 3 min, after which the solvent was removed. 10 ml of a deprotection solution (20% piperidine/DMF) were added to the reactor and agitation for 10 min at room temperature and solution removal were performed. After adding the same volume of the deprotection solution, the reaction was undertaken for 10 min and solution was removed, followed by washing sequentially with DMF, MC and DMF. 10 ml of DMF solution was added to a new reactor and then 2 mmole of Fmoc-Gln(trt)-OH, 2 mmole of HoBt and 2 mmole of Bop were added, followed by agitation for solubilization. 4 mmole of DIEA was added to the reactor and agitation was carried out to dissolve all solid contents. The dissolved amino acid solution was introduced into the reactor containing the deprotected resin and reaction was undertaken with agitating for 1 hr at room temperature. Following the removal of the reaction solution, the resultant was agitated three times with DMF solution to remove unreacted residuals. The reacted resin was taken to evaluate extent of reactions by Ninhydrine test. Using the 20% piperidine/DMF solution, the deprotection was performed twice in the same manner as described above to yield Gln(trt)-Rink amide resin. After washing with DMF and MC, Ninhydrine test was carried out and the attachments of amino acids were performed as described above. Based on the amino acid sequence designed by the present inventors, Fmoc-Glu(tBu)-OH, Fmoc-Thr(tBu)-OH, Fmoc-Lys(Boc)-OH, Fmoc-Lys(Boc)-OH, Fmoc-Leu-OH and Fmoc-Lys(Boc)-OH were attached to resins. The prepared peptidyl resin was washed three times with DMF, MC and methanol, respectively and dried under nitrogen atmosphere, after which it was vacuum-dried under $P_2O_5$, finally giving Fmoc-Lys(Boc)-Leu-Lys(Boc)-Lys(Boc)-Thr(tBu)-Glu(tBu)-Thr(tBu)-Gln(trt)-Rink amide resin.

Example 1

Synthesis of Fmoc-Octapeptide (Fmoc-Lys-Leu-Lys-Lys-Thr-Glu-Thr-Gln-OH)

Fmoc-Lys(Boc)-Leu-Lys(Boc)-Lys(Boc)-Thr(tBu)-Glu(tBu)-Thr(tBu)-Gln(trt)-CTL resins prepared in Synthesis Example 1 were incubated with a solution consisting of TFA, TIS and water (TFA:TIS:water, 95:2.5:2.5) for 1 hr. The resins were filtered and washed with a small volume of TFA solution, after which the filtrate was combined with the mother liquor. After distillation under reduced pressure to reduce the total volume by two, the precipitation was induced using cold ether and the formed precipitates were collected by centrifugation, followed by washing twice with cold ether. The resultant was dried under nitrogen atmosphere to provide 1.1 g of unpurified Fmoc-Octapeptide (Fmoc-KLKKTETQ) (yield 91.9%). The molecular weight of the final product was measured as 1198.5 (theoretical MW 1197.4) using a molecular weight analyzer.

Example 2

Synthesis of Ac-Octapeptide (Ac-Lys-Leu-Lys-Lys-Thr-Glu-Thr-Gln-OH)

Fmoc-Lys(Boc)-Leu-Lys(Boc)-Lys(Boc)-Thr(tBu)-Glu(tBu)-Thr(tBu)-Gln(trt)-CTL resins prepared in Synthesis Example 1 were swelled using DMF and reacted twice with the 20% piperidine/DMF solution for 10 min to remove Fmoc-protecting group. 2 ml of acetic acid anhydride, 610 mg of HoBt and 1.77 g of Bop were introduced into a new reactor, and then 1.56 ml of DIEA was added to the reactor, followed by agitating. Pre-made acetic acid anhydride was introduced into the reactor containing the resin and the reaction was undertaken for 30 min. The resin was washed three times sequentially with DMF, MC and methanol and completely dried. The dried peptidyl resin was added to a round bottom flask and reacted with 30 ml of the leaving solution [containing 95% TFA, 2.5% distilled water and 2.5% thioanisole] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 0.93 g of unpurified acetyl-octapeptide (Ac-KTKKTETQ) (yield 91.4%).

Figure 3:
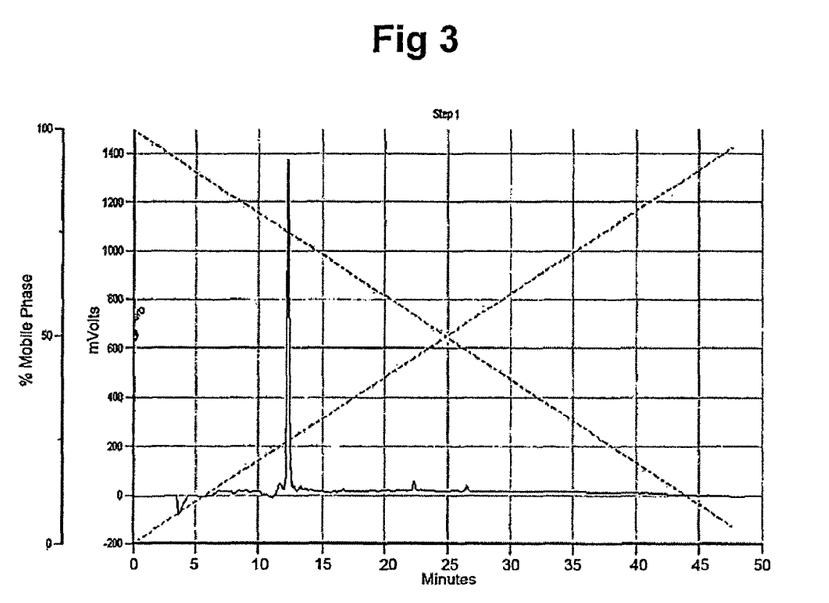
FIG. 3 represents results of high performance liquid chromatography analysis of the acetyl-octapeptide prepared in Example.
Figure 4:
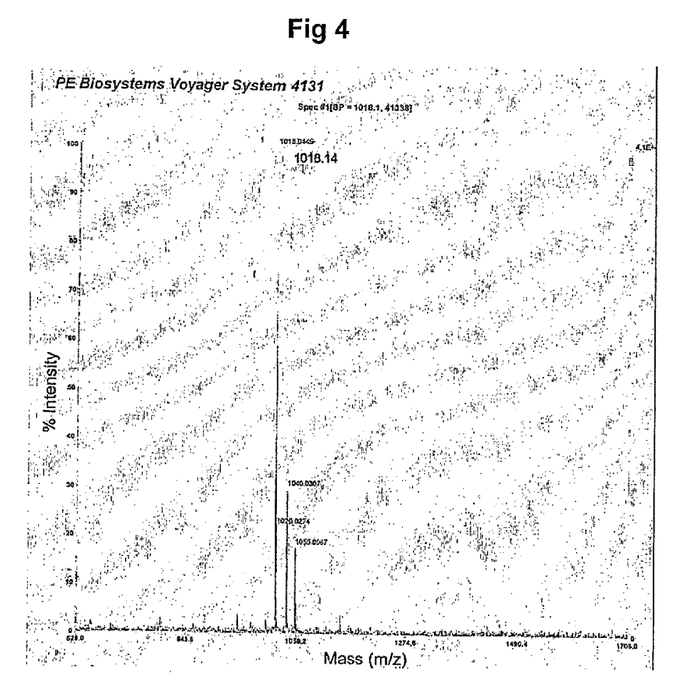
FIG. 4 represents results of mass spectroscopy analysis of the acetyl-octapeptide prepared in Example.

The unpurified peptides were fractionated using a high performance liquid chromatography, and major peptides were collected and subjected to distillation to remove acetonitrile, followed by lyophilization to give 0.72 g of purified peptides of interest. The finally prepared peptide was analyzed using high performance liquid chromatography to show 96% purity (FIG. 3). The final yield was 70.9%. The molecular weight of the final product was measured as 1018.0 (theoretical MW 1017.2) using a mass analyzer, demonstrating that the peptide of interest, Ac-KTKKTETQ was successfully synthesized (FIG. 4).

Example 3

Synthesis of Formyl-Octapeptide (Formyl-Lys-Leu-Lys-Lys-Thr-Glu-Thr-Gln-OH)

Fmoc-Lys(Boc)-Leu-Lys(Boc)-Lys(Boc)-Thr(tBu)-Glu(tBu)-Thr(tBu)-Gln(trt)-CTL resins prepared in Synthesis Example 1 were swelled using DMF and reacted twice with the 20% piperidine/DMF solution for 10 min to remove Fmoc-protecting group. 2 ml of acetic acid anhydride, 610 mg of HoBt and 1.77 g of Bop were introduced into a new reactor, and then 1.56 ml of DIEA was added to the reactor, followed by agitating. Pre-made acetic acid anhydride was introduced into the reactor containing the resin and the reaction was undertaken for 30 min. The resin was washed three times sequentially with DMF, MC and methanol and completely dried. The dried peptidyl resin was added to a round bottom flask and reacted with 30 ml of the leaving solution [containing 95% TFA, 2.5% distilled water and 2.5% thioanisole] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 0.88 g of unpurified formyl-octapeptide (Formyl-KTKKTETQ) (yield 87.7%). The molecular weight of the final product was measured as 1003.6 (theoretical MW 1003.2) using a molecular weight analyzer.

Example 4

Synthesis of Palmitoyl-Octapeptide (Palmitoyl-Lys-Leu-Lys-Lys-Thr-Glu-Thr-Gln-OH)

Fmoc-Lys(Boc)-Leu-Lys(Boc)-Lys(Boc)-Thr(tBu)-Glu(tBu)-Thr(tBu)-Gln(trt)-CTL resins prepared in Synthesis Example 1 were swelled using DMF and reacted twice with the 20% piperidine/DMF solution for 10 min to remove Fmoc-protecting group. 1.5 mmol palmitoyl chloride in 5 ml DMF and 1.56 ml of DIPEA were introduced the reactor containing the resin and reaction was carried out for 1 hr at 35° C. The resultant was washed three times with 30 ml DMF and four times with 30 ml DCM and dried under nitrogen atmosphere and then dried using $P_2O_5$ under reduced pressure, yielding decapeptides having side chains protected with palmitoyl groups. 1 g of the dried peptidyl resin was added to a round bottom flask and reacted with 30 ml of the leaving solution [containing 95% TFA, 2.5% distilled water and 2.5% thioanisole] for 1 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.4 g of unpurified palmitoyl-decapeptide (Palmitoyl-KTKKTETQ) (yield 113.9%). The molecular weight of the final product was measured as 1230.2 (theoretical MW 1229.6) using a molecular weight analyzer.

Examples 5 and 6

Synthesis of Stearyl-Octapeptide (Stearyl-Lys-Leu-Lys-Lys-Thr-Glu-Thr-Gln-OH) and Myristyl-Octapeptide (Myristyl-Lys-Leu-Lys-Lys-Thr-Glu-Thr-Gln-OH)

Fmoc-Lys(Boc)-Leu-Lys(Boc)-Lys(Boc)-Thr(tBu)-Glu(tBu)-Thr(tBu)-Gln(trt)-CTL resins prepared in Synthesis Example 1 were divided into two batches and reacted twice with the 20% piperidine/DMF solution for 10 min to remove Fmoc-protecting group. 1.5 mmol myristyl chloride in 5 ml DMF (myristyl-decapeptide) or 1.5 mmol stearyl chloride in 5 ml DMF (stearyl-decapeptide) and 1.56 ml of DIPEA were introduced the reactor containing the resin and reaction was carried out for 1 hr at 35° C. The resultant was washed three times with 30 ml DMF and four times with 30 ml DCM and dried under nitrogen atmosphere and then dried using $P_2O_5$ under reduced pressure, yielding decapeptides having side chains protected with myristyl or stearyl groups. 1 g of the dried peptidyl resin was added to a round bottom flask and reacted with 10 ml of the leaving solution (containing 81.5% TFA, 5% distilled water, 5% thioanisole, 5% phenol, 2.5% EDT and 1% TIS) for 1 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.01 g of unpurified myristyl-decapeptide (Myristyl-KTKKTETQ) (yield 84.1%) and 1.1 g of unpurified stearyl-decapeptide (Stearyl-KTKKTETQ) (yield 87.5%). The molecular weights of the final products were measured as 1202.4 (theoretical MW 1201.5) for myristyl-decapeptide and 1258.5 (theoretical MW 1257.7) for stearyl-decapeptide using a molecular weight analyzer.

Example 7

Synthesis of Fmoc-Octapeptide (Fmoc-Lys-Leu-Lys-Lys-Thr-Glu-Thr-Gln-NH$_2$)

Fmoc-Lys(Boc)-Leu-Lys(Boc)-Lys(Boc)-Thr(tBu)-Glu(tBu)-Thr(tBu)-Gln(trt)-Rink amide resins prepared in Synthesis Example 2 were incubated with a solution consisting of TFA, TIS and water (TFA:TIS:water, 95:2.5:2.5) for 1 hr. The resins were filtered and washed with a small volume of TFA solution, after which the filtrate was combined with the mother liquor. After distillation under reduced pressure to reduce the total volume by two, the precipitation was induced using cold ether and the formed precipitates were collected by centrifugation, followed by washing twice with cold ether. The resultant was dried under nitrogen atmosphere to provide 0.98 g of unpurified Fmoc-Octapeptide (Fmoc-KLKKTETQ-NH$_2$) (yield 81.9%). The molecular weight of the final product was measured as 1196.9 (theoretical MW 1196.4) using a molecular weight analyzer.

Example 8

Synthesis of Ac-Octapeptide (Ac-Lys-Leu-Lys-Lys-Thr-Glu-Thr-Gln-NH$_2$)

Fmoc-Lys(Boc)-Leu-Lys(Boc)-Lys(Boc)-Thr(tBu)-Glu(tBu)-Thr(tBu)-Gln(trt)-Rink amide resins prepared in Synthesis Example 2 were swelled using DMF and reacted twice with the 20% piperidine/DMF solution for 10 min to remove Fmoc-protecting group. 2 ml of acetic acid anhydride, 610 mg of HoBt and 1.77 g of Bop were introduced into a new reactor, and then 1.56 ml of DIEA was added to the reactor, followed by agitating. Pre-made acetic acid anhydride was introduced into the reactor containing the resin and the reaction was undertaken for 30 min. The resin was washed three times sequentially with DMF, MC and methanol and completely dried. The dried peptidyl resin was added to a round bottom flask and reacted with 30 ml of the leaving solution [containing 95% TFA, 2.5% distilled water and 2.5% thioanisole] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 0.87 g of unpurified acetyl-octapeptide (Ac-KTKKTETQ-NH$_2$) (yield 85.6%).

The unpurified peptides were fractionated using a high performance liquid chromatography, and major peptides were collected and subjected to distillation to remove acetonitrile, followed by lyophilization to give 0.72 g of purified peptides of interest. The finally prepared peptide was analyzed using high performance liquid chromatography to show 96% purity. The final yield was 70.9%. The molecular weight of the final product was measured as 1016.9 (theoretical MW 1016.2) using a mass analyzer, demonstrating that the peptide of interest, Ac-KTKKTETQ-NH$_2$ was successfully synthesized.

Example 9

Synthesis of Formyl-Octapeptide (Formyl-Lys-Leu-Lys-Lys-Thr-Glu-Thr-Gln-NH$_2$)

Fmoc-Lys(Boc)-Leu-Lys(Boc)-Lys(Boc)-Thr(tBu)-Glu(tBu)-Thr(tBu)-Gln(trt)-Rink amide resins prepared in Synthesis Example 2 were swelled using DMF and reacted twice with the 20% piperidine/DMF solution for 10 min to remove Fmoc-protecting group. 2 ml of acetic acid anhydride, 610 mg of HoBt and 1.77 g of Bop were introduced into a new reactor, and then 1.56 ml of DIEA was added to the reactor, followed by agitating. Pre-made acetic acid anhydride was introduced into the reactor containing the resin and the reaction was undertaken for 30 min. The resin was washed three times sequentially with DMF, MC and methanol and completely dried. The dried peptidyl resin was added to a round bottom flask and reacted with 30 ml of the leaving solution [containing 95% TFA, 2.5% distilled water and 2.5% thioanisole] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 0.89 g of unpurified formyl-octapeptide (Formyl-KTKKTETQ-NH$_2$) (yield 88.8%). The molecular weight of the final product was measured as 1002.8 (theoretical MW 1002.2) using a molecular weight analyzer.

Example 10

Synthesis of Palmitoyl-Octapeptide (Palmitoyl-Lys-Leu-Lys-Lys-Thr-Glu-Thr-Gln-NH$_2$)

Fmoc-Lys(Boc)-Leu-Lys(Boc)-Lys(Boc)-Thr(tBu)-Glu(tBu)-Thr(tBu)-Gln(trt)-Rink amide resins prepared in Synthesis Example 2 were swelled using DMF and reacted twice with the 20% piperidine/DMF solution for 10 min to remove Fmoc-protecting group. 1.5 mmol palmitoyl chloride in 5 ml DMF and 1.56 ml of DIPEA were introduced the reactor containing the resin and reaction was carried out for 1 hr at 35° C. The resultant was washed three times with 30 ml DMF and four times with 30 ml DCM and dried under nitrogen atmosphere and then dried using P$_2$O$_5$ under reduced pressure, yielding decapeptides having side chains protected with palmitoyl groups. 1 g of the dried peptidyl resin was added to a round bottom flask and reacted with 30 ml of the leaving solution [containing 95% TFA, 2.5% distilled water and 2.5% thioanisole] for 1 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.3 g of unpurified palmitoyl-decapeptide (Palmitoyl-KTKKTETQ-NH$_2$) (yield 105.8%). The molecular weight of the final product was measured as 1229.4 (theoretical MW 1228.6) using a molecular weight analyzer.

Examples 11 and 12

Synthesis of Stearyl-Octapeptide (Stearyl-Lys-Leu-Lys-Lys-Thr-Glu-Thr-Gln-NH$_2$) and Myristyl-Octapeptide (Myristyl-Lys-Leu-Lys-Lys-Thr-Glu-Thr-Gln-NH$_2$)

Fmoc-Lys(Boc)-Leu-Lys(Boc)-Lys(Boc)-Thr(tBu)-Glu(tBu)-Thr(tBu)-Gln(trt)-Rink amide resins prepared in Synthesis Example 2 were divided into two batches and reacted twice with the 20% piperidine/DMF solution for 10 min to remove Fmoc-protecting group. 1.5 mmol myristyl chloride in 5 ml DMF (myristyl-decapeptide) or 1.5 mmol stearyl chloride in 5 ml DMF (stearyl-decapeptide) and 1.56 ml of DIPEA were introduced the reactor containing the resin and reaction was carried out for 1 hr at 35° C. The resultant was washed three times with 30 ml DMF and four times with 30 ml DCM and dried under nitrogen atmosphere and then dried using $P_2O_5$ under reduced pressure, yielding decapeptides having side chains protected with myristyl or stearyl groups. 1 g of the dried peptidyl resin was added to a round bottom flask and reacted with 10 ml of the leaving solution (containing 81.5% TFA, 5% distilled water, 5% thioanisole, 5% phenol, 2.5% EDT and 1% TIS) for 1 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 0.98 g of unpurified myristyl-decapeptide (Myristyl-KTKKTETQ-NH$_2$) (yield 81.6%) and 1.02 g of unpurified stearyl-decapeptide (Stearyl-KTKKTETQ-NH$_2$) (yield 81.2%). The molecular weights of the final products were measured as 1201.4 (theoretical MW 1200.5) for myristyl-decapeptide and 1257.2 (theoretical MW 1256.7) for stearyl-decapeptide using a molecular weight analyzer.

Example 13

Preparation of Nano Peptides 50 mg of the acetyl decapeptide synthesized in Example 2 was dissolved in 500 ml of distilled water. The peptide solution was mixed with 5 g lecithin, 0.3 ml sodium oleate, 50 ml ethanol and a small amount of oils and its volume was adjusted with distilled water to 1 L. The resulting solution was subjected to a microfluidizer under high pressure for emulsification, thereby providing nanosomes having 100-nm size. The nanosomes were prepared to have a final concentration of about 50 ppm and used as ingredients for cosmetics.

Formulation Example 1

Skin Softener

A skin softener containing nanosomes of acetyl decapeptide prepared in Example 13 was formulated according to the following composition.

TABLE 1

| Ingredients | Content (wt %) |
| --- | --- |
| Acetyl-octapeptide | 0.001 |
| 1,3-butylene glycol | 6.0 |
| Glycerine | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Example 2

Nutrient Cream

A nutrient cream containing nanosomes of acetyl decapeptide prepared in Example 13 was formulated according to the following composition.

TABLE 2

| Ingredients | Content (wt %) |
| --- | --- |
| Acetyl-octapeptide | 0.001 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerine | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Nutrient Liquid

A nutrient liquid containing nanosomes of acetyl decapeptide prepared in Example 13 was formulated according to the following composition.

TABLE 3

| Ingredients | Content (wt %) |
| --- | --- |
| Acetyl-octapeptide | 0.002 |
| 1,3-butylene glycol | 4.0 |
| Glycerine | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |
| Preservative, pigments | Proper amount |
| Perfume | Proper amount |
| Distilled water | Residual amount |
| Total | 100 |

Formulation Example 4

Essence

An essence containing nanosomes of acetyl decapeptide prepared in Example 13 was formulated according to the following composition.

TABLE 4

| Ingredients | Content (wt %) |
| --- | --- |
| Acetyl-octapeptide | 0.005 |
| Glycerine | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Formulation Examples 5-7

Hair Toner

A hair toner containing the acetyl decapeptide prepared and purified in Example 2 was formulated according to the following composition.

TABLE 5

| Ingredients | Formulation Example 5 | Formulation Example 6 | Formulation Example 7 |
| --- | --- | --- | --- |
| Acetyl-octapeptide | 0.05 | 0.005 | 0.005 |
| Pseudoceramide | 0.05 | 0.2 | 0.48 |
| Hydroxyethyl cellulose | 0.3 | 0.1 | — |
| Glyceryl monostearate | 0.4 | 0.5 | 0.3 |
| Propylene glycol | 2.0 | 1.0 | 1.5 |
| Silicone oil | 0.5 | 1.0 | 0.5 |
| Cetostearyl alcohol | 1.5 | 2.2 | 0.5 |
| Orange wax | 0.1 | 0.5 | 3.0 |
| Distearyldimethyl ammonium chloride | 1.0 | 2.0 | 1.0 |
| Cetyltrimethyl ammonium chloride | 1.0 | — | 1.5 |
| POE alkylether/stearyl alcohol | 0.5 | 1.0 | 3.0 |
| Perfume, | Proper amount | Proper amount | Proper amount |
| Preservative | Proper amount | Proper amount | Proper amount |
| Distilled water | Residual amount | Residual amount | Residual amount |
| Total | 100 | 100 | 100 |

Experimental Example 1

Measurement of Biological Activities

The biological activities of the purified acetyl-octapeptide of Example 2 were evaluated using BALB/MK karatinocytes according to Falco et al method to measure [$^3$H]-thymidine incorporation (Falco, et al. (1988) *Oncogene.*, 2, 573). BALB/MK karatinocytes were cultured in 250 ml-flasks containing EMEM (Eagle's minimal essential media, Gibco, U.S.A.) supplemented with 100% FBS (fetal bovine serum). BALB/MK karatinocytes cultured were treated with 0.25% trypsin solution to detach cells from the bottom of culture flasks and centrifuged to collect cell pellets. Cells were resuspended in EMEM not containing FBS, its aliquot, 2×10$^4$ cells/0.3 ml medium was added to each well of 24-well plates and cultured under 7% $CO_2$ for 24 hr at 37° C. 2 ng/ml of the acetyl octapeptide prepared in Example 2 was serially diluted by two-fold using EMEM containing 0.2 (w/v) % bovine serum albumin and 0.3 ml of the diluted peptide was added to each well, followed by additional culturing under 7% $CO_2$ for 6 hr at 37° C. Afterwards, 0.5 μCi of [$^3$H]-thymidine (Amersham, TRK 686, 68 Ci/mmol) was added to each well and incubated overnight. After removing supernatants, cells were washed once using PBS (phosphate buffered saline) and incubated with 0.1 ml of 0.25% trypsin solution for 5 min at 37° C. to detach cells from the bottom of plates. 0.5 ml of EMEM containing 10% FBS was added to each well and cells were adhered to glass fiber filters using a cell harvester (12 well cell harvester, Millipore, U.S.A.). The filters were washed once with 1 ml of distilled water and once with 1 ml of ethanol, and kept to stand for 30 min at 60° C. for drying. The dried filters were added along with 2 ml of scintillation cocktail to scintillation vials and allowed to stand for 30 min at room temperature, after which radioactivity incorporated into cells was determined using a scintillation counter (Beckman, U.S.A) as shown in FIG. 5.

Figure 5:
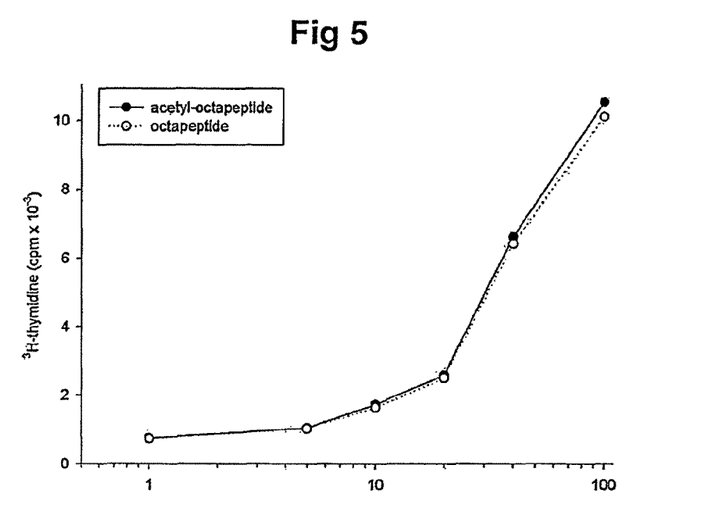
FIG. 5 represents measurement results of biological activities of the octapeptide and the acetyl-octapeptide of this invention.

As represented in FIG. 5, the acetyl octapeptide of this invention promotes thymidine incorporation into kerationcytes in a dose-dependent fashion. Therefore, it could be appreciated that the acetyl octapeptide of this invention has high biological activities similar to intact Tβ-4F.

Experimental Example 2

Evaluation of Stability

Figure 6:
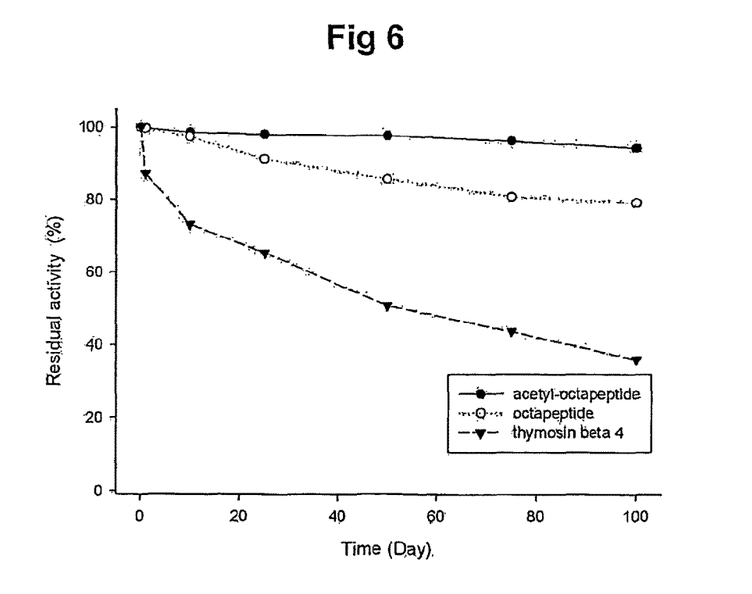
FIG. 6 represents analysis results of stability of the acetyl-octapeptide.

To evaluate stability of the purified acetyl octapeptide, the octapeptide and acetyl decapeptide were dissolved in 50 mM Tris-HCl (pH 8.0) to a concentration of 10 μg/ml. A recombinant thymosin β-4 produced *E. coli* was prepared as a control in the same buffer to a concentration of 1 μg/ml. The prepared solutions were introduced into glass vials and kept to stand at 37° C. Afterwards, the solutions were taken on days 0, 1, 10, 25, 50, 75 and 100 and subjected to [³H]-thymidine incorporation using BALB/MK karatinocytes to determine residual activities of peptides and recombinant thymosin β-4 (FIG. 6). The results were given as relative values to the activity (100%) of sample taken on day 0.

As represented in FIG. 6, the activity of the natural-occurring thymosin β-4 was sharply decreased with the lapse of time. In contrast, the activity of the present octapeptide was shown not to be decreased over time. In particular, the acetyl octapeptide having the N-terminal protected with acetyl groups showed excellent stability.

Experimental Example 3

Analysis of Effects of Peptides on Growth of HaCaT Keratinocytes

Figure 7:
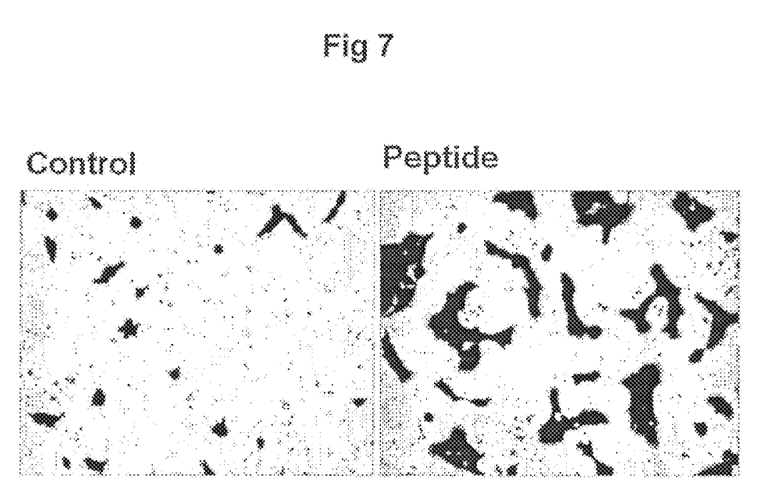
FIG. 7 is a microscope image demonstrating promotion activity of the acetyl-octapeptide to the growth of human keratinocytes.
Figure 8:
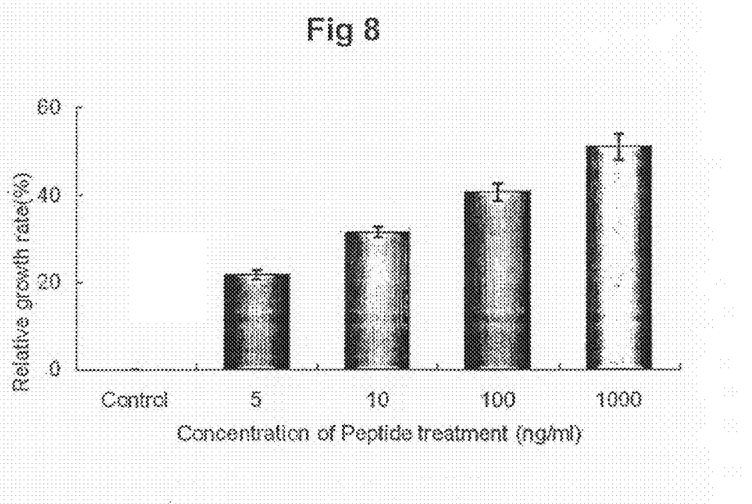
FIG. 8 represents influence of the acetyl-octapeptide on the growth rate of human keratinocytes.

To analyze effects of peptides of this invention on proliferation of keratinocytes, SRB (Sulforhodamine B) colorimetric assay was carried out using HaCaT kerationcyte according to Rizzino et al method (Rizzino, et al. *Cancer Res.*, 48:4266 (1988)). HaCaT ketatinocytes (The Korean Cell Line Bank) were cultured in 250 ml-flasks containing EMEM (Eagle's minimal essential media, Gibco, U.S.A.) supplemented with 100% FBS (fetal bovine serum). HaCaT ketatinocytes cultured were treated with 0.25% trypsin solution to detach cells from the bottom of culture flasks and centrifuged to collect cell pellets. Cells were resuspended in EMEM not containing FBS, its aliquot ($4\times10^3$) cells was added to each well of 96-well plates and cultured under 7% $CO_2$ for 24 hr at 37° C. After 24-hr culture, the medium was changed with a fresh medium not containing serum and cells were incubated with thymosin β-4 or the acetyl-octapeptide (10 ng/ml or 1,000 ng/ml) dissolved in 10% DMSO for 72 hr under the same conditions as described above. After removing supernatants, cells were washed once using PBS (phosphate buffered saline) and incubated with SRB solution (Sigma-Aldrich). Cells were washed with PBS and observed under a microscope to find cell viability. In addition, absorbance at 590 nm was measured to analyze cell proliferation (FIG. 7). FIG. 8 is images of microscope to represent viability of cells treated with peptides for 72 hr.

Figure 9:
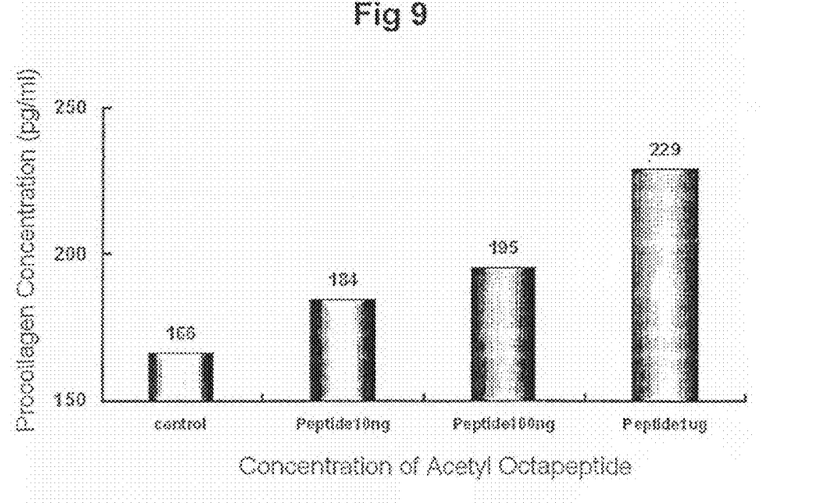
FIG. 9 represents graphs to show the increase in procollagen level where culturing cells with the acetyl-octapeptide.
Figure 10:
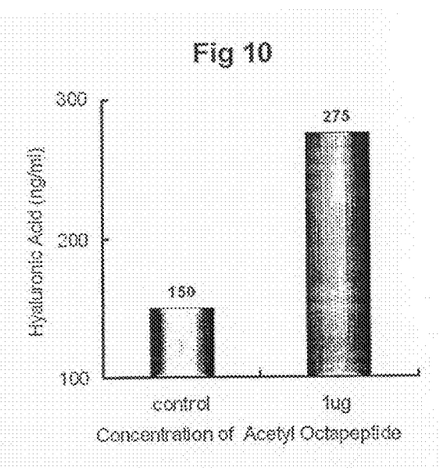
FIG. 10 represents graphs to show the increase in hyaluronic acid levels where culturing cells with the acetyl-octapeptide.

Furthermore, HaCaT cell line was treated with the acetyl-octapeptide of this invention (1 μg/ml) and the level of procollagen, one of indicators to show the improvement in skin wrinkle, was examined (FIG. 9). The level of procollagen was measured using Procollagen ELISA kit (Takara). For verifying effects on levels of hyaluronic acid, another indicator representing the improvement in skin wrinkle, HaCaT cell line was incubated with the acetyl-octapeptide of this invention (5 μmole) and the level of hyaluronic acid was measured using Hyaluronic acid ELISA kit (Echelon Biosciences Inc, USA) (FIG. 10).

As shown in FIGS. 7 and 8, the peptide of this invention contributed to much higher cell viability than control. Where HaCaT keratinocytes were treated with the present peptide, the levels of procollagen and hyaluronic acid in cells was increased in a dose-dependent manner (FIGS. 9 and 10).

Accordingly, these results urge us to reason that the peptides of this invention exhibit significant efficacies to improve skin wrinkle.

Experimental Example 4

Analysis of Effects of Peptides on Skin Thickness

For evaluating applicability to cosmetics and in vivo efficacies of the peptides of this invention, the cosmetic formulation was applied onto mouse skin.

6-old-week Balb C male mice (Central Lab. Animal, Inc., Korea) were subjected to one-week stabilization and hairs of their back were partially removed using thioglycolic acid-containing cream. Mice were divided into two groups; one group of which was topically administered with the cream comprising acetyl decapeptide-containing nanosomes and the other group of which was topically administered with nanosome-containing Formulation Example 2 comprising the acetyl octapeptide. The application was performed every morning (A.M. 8:30) and evening (P.M. 6:00) for 5 days in the dose of 100 mg. After the application, mice were sacrificed by cervical dislocation and their skin tissues were paraffinized. Paraffinized tissues were sectioned using a microtomb in a thickness of 8 μm and were stained with hematoxyline/eosin, followed by observation under an optical microscope (FIG. 11).

Figure 11:
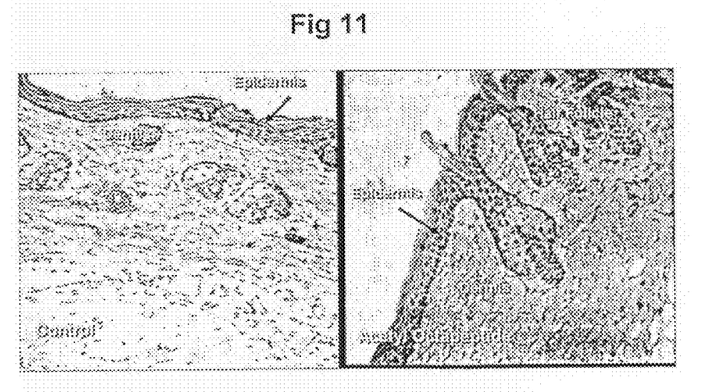
FIG. 11 is a microscope image to show the change in skin thickness of Balb C mice administered with cosmetics containing the acetyl-octapeptide.

As represented in FIG. 11, the nanosome cosmetics comprising the acetyl octapeptide of this invention allowed to promote the formation and growth of keratinocyte layer and epidermal layer. Accordingly, it could be recognized that cosmetics comprising peptides of this invention exert the improvements in skin wrinkle and elasticity.

Experimental Example 5

Analysis of Hair-Growth Activities

The hairs of the back portions of C3H/HeN mice were completely removed using a hair cutter and a hair loss-inducing substance. One day later, Formulation Example 5 (cosmetic liquid) was applied onto the back portions for 25 days and then hair growth was observed.

Figure 12:
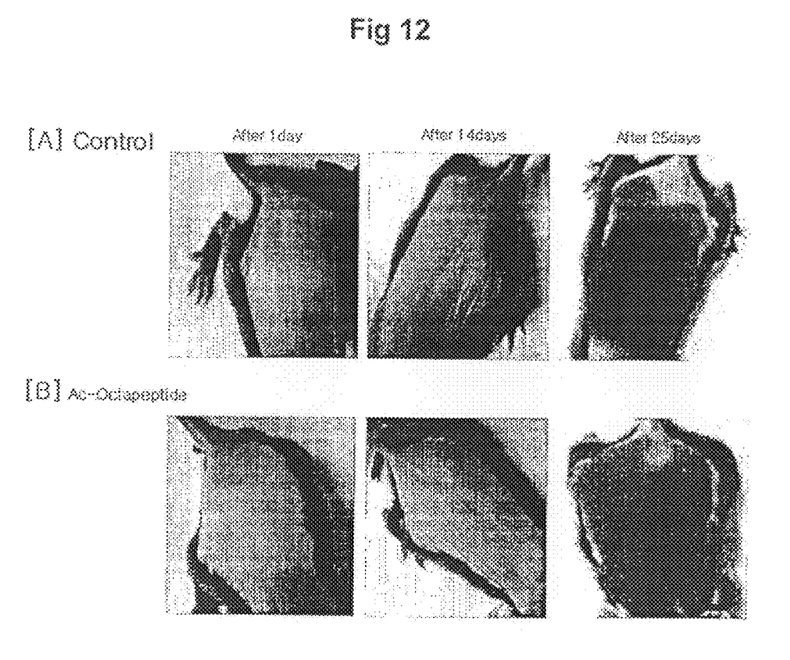
FIG. 12 is a photograph showing effects of the acetyl-octapeptide on hair growth of mice.

As a result, it was found that the hair growth of mice treated with the peptide of this invention was increased by 25-30% compared with control in considering initial hair growth effects and hair length and number, as shown in FIG. 12.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method of increasing the level of procollagen or hyaluronic acid in skin tissue, or promoting keratinocyte proliferation, keratinocyte layer formation or epidermal layer formation, comprising administering to a subject in need thereof a composition comprising a peptide consisting of the amino acid sequence of SEQ ID NO:1 as an active ingredient.

2. The method according to claim 1, wherein the composition is a pharmaceutical composition comprising (a) a pharmaceutically effective amount of the peptide consisting of the amino acid sequence of SEQ ID NO:1; and (b) a pharmaceutically acceptable carrier.

3. The method according to claim 1, wherein the composition is a cosmetic composition comprising (a) a cosmetically effective amount of the peptide consisting of the amino acid sequence of SEQ ID NO:1; and (b) a cosmetically acceptable carrier.

4. The method according to claim 1, wherein the subject is in need of improvement in a skin condition.

5. The method according to claim 4, wherein the improvement in the skin condition is the improvement in wrinkle or skin elasticity, the prevention of skin aging, the treatment of atopic condition, the improvement in skin moisture, the removal of dark spots or the treatment of acne.

6. The method according to claim 5, wherein the improvement in the skin condition is the improvement in wrinkle.

7. The method according to claim 1, wherein the C-terminal of the peptide is modified with a hydroxyl group (—OH) or amino group (—NH$_2$).

8. The method according to claim 1, wherein the N-terminal of the peptide is protected with a protection group selected from the group consisting of acetyl group, fluorenyl methoxy carbonyl (Fmoc) group, formyl group, palmitoyl group, myristyl group, stearyl group and polyethylene glycol (PEG).

* * * * *

SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence

```
-continued

<220> FEATURE:
<223> OTHER INFORMATION: thymosin beta-4 mimicking peptide

<400> SEQUENCE: 1

Lys Leu Lys Lys Thr Glu Thr Gln
 1               5

<210> SEQ ID NO 2
<211> LENGTH: 42
<212> TYPE: PRT
<213> ORGANISM: Homo sapiens

<400> SEQUENCE: 2

Ser Asp Lys Pro Asp Met Ala Glu Ile Glu Lys Phe Asp Lys Ser Lys
 1               5                   10                  15

Leu Lys Lys Thr Glu Thr Gln Glu Lys Asn Pro Leu Pro Ser Lys Glu
            20                  25                  30

Thr Ile Glu Gln Glu Lys Gln Ala Gly Glu
            35                  40
```